(12) United States Patent
Belotserkovsky

(10) Patent No.: US 9,084,571 B2
(45) Date of Patent: Jul. 21, 2015

(54) URINE FLOW MONITORING DEVICE AND METHOD

(71) Applicant: Edward Belotserkovsky, San Francisco, CA (US)

(72) Inventor: Edward Belotserkovsky, San Francisco, CA (US)

(*) Notice: Subject to any disclaimer, the term of this patent is extended or adjusted under 35 U.S.C. 154(b) by 13 days.

(21) Appl. No.: 14/025,826

(22) Filed: Sep. 13, 2013

(65) Prior Publication Data

US 2014/0018702 A1 Jan. 16, 2014

Related U.S. Application Data

(60) Division of application No. 13/041,416, filed on Mar. 6, 2011, now Pat. No. 8,567,258, and a continuation-in-part of application No. 12/877,289, filed on Sep. 8, 2010, now Pat. No. 8,276,465.

(51) Int. Cl.
| | |
|---|---|
| *G01F 1/66* | (2006.01) |
| *G01N 29/24* | (2006.01) |
| *A61B 5/20* | (2006.01) |
| *A61B 7/00* | (2006.01) |
| *A61B 5/00* | (2006.01) |

(52) U.S. Cl.
CPC . *A61B 5/208* (2013.01); *A61B 7/00* (2013.01); *A61B 5/6889* (2013.01); *A61B 5/6891* (2013.01); *A61B 5/6898* (2013.01); *A61B 2562/0204* (2013.01)

(58) Field of Classification Search
USPC .............................................. 73/861.18, 861
See application file for complete search history.

(56) References Cited

U.S. PATENT DOCUMENTS

| | | | | | |
|---|---|---|---|---|---|
| 5,377,101 | A | * | 12/1994 | Rollema ........................ | 600/584 |
| 6,002,966 | A | * | 12/1999 | Loeb et al. ..................... | 607/57 |
| 6,195,585 | B1 | * | 2/2001 | Karunasiri et al. ............. | 607/57 |
| 7,194,369 | B2 | * | 3/2007 | Lundstedt et al. ............. | 702/104 |
| 7,811,237 | B2 | * | 10/2010 | Brohan et al. ................ | 600/584 |
| 8,054,989 | B2 | * | 11/2011 | Paik ................................ | 381/86 |
| 8,231,552 | B2 | * | 7/2012 | Shahar et al. ................. | 600/586 |
| 2003/0097039 | A1 | * | 5/2003 | Besson et al. .................. | 600/29 |
| 2008/0275366 | A1 | * | 11/2008 | Brohan et al. ................. | 600/584 |

* cited by examiner

*Primary Examiner* — Lisa Caputo
*Assistant Examiner* — Jamel Williams
(74) *Attorney, Agent, or Firm* — Cascio & Zervas

(57) ABSTRACT

Unique characteristic sounds produced as urine impacts the surface of the water are used to monitor men's urinary flow patterns and their dynamics. By detecting the intensity at selected acoustic frequencies, it is possible to accurately and precisely measure the urine flow rate. Techniques for analyzing urine flow and its dynamics employ sound levels that are detected with digital filters at two or more distinct frequency regions or channels of the sound spectrum. One frequency region that is designated the measurement channel is where the sound measurement intensity strongly depends on urine flow levels. Another frequency region that is designated the reference channel is where the sound measurement intensity is not dependent on urine flow levels. By using a combination of measurements from the measurement channel and the reference channel, the urine flow monitoring apparatus compensates for variations in operating conditions and other factors during use.

23 Claims, 7 Drawing Sheets

URINE FLOW MONITORING DEVICE AND METHOD

REFERENCE TO RELATED APPLICATIONS

This application is a divisional application of U.S. patent application Ser. No. 13/041,416 that was filed on Mar. 6, 2011, which was a continuation-in-part application of application Ser. No. 12/877,289 that was filed on Sep. 8, 2010, now U.S. Pat. No. 8,276,465, and claimed priority to U.S. provisional application 61/353,216 that was filed on Jun. 10, 2010.

FIELD OF THE INVENTION

The present invention generally relates to a medical apparatus for monitoring the discharge of urine by an individual. The apparatus gauges the volumetric flow and flow dynamics of the discharge, analyzes the data and displays the results.

BACKGROUND OF THE INVENTION

The prostate is a gland of the male reproductive system that is located in front of the rectum and just below the bladder. The prostate, comprised largely of muscular and glandular tissue, is wrapped around the urethra, which carries urine from the bladder out through the tip of the penis. Disorders of the prostate are fairly common during the aging, process and include prostatitis, benign prostatic hyperplasia (BPH), and adenoma of the prostate, or prostate cancer. Prostatitis, which may or may not be the result of an infection, is generally defined as an inflammation of the prostate. Symptoms associated with prostatitis are pain, voiding symptoms such as nocturia, frequency and urgency of urination, incomplete voiding, and decreased force and/or intermittency of the urinary stream, impotence, and infertility, Benign prostatic hyperplasia (BPH) is a noncancerous enlargement of the prostate and is common in men over age 40. Symptoms associated with BPH are similar to those observed with prostatitis. Prostate cancer, i.e., adenocarcinoma of the prostate, is the most common malignancy in men greater than 50 years in the U.S. The incidence increases with each decade of life. Prostate cancer is generally slowly progressive and may cause no symptoms. In late disease, symptoms of bladder outlet obstruction, urethral obstruction, and hematuria may appear and metastasis to the bone may occur.

Diagnosis of urological disorders is often facilitated by a patient's urine flow rate data. Urological disorders such as an obstruction in the lower urological tract or neurotic bladder can be detected by studying the patient's urine flow rate as it varies from the beginning of voiding to the end and the total volume of urine voided. This data can be compared to the mean data for an individual of the same sex and age to help determine the degree of urethral stricture.

Urine flow data is also useful in diagnosing prostrate enlargement. Prostrate enlargement usually occurs gradually with no noticeable impairment to the patient. Merely observing the patient void will usually not enable the urologist or physician to accurately assess the degree of prostate enlargement. However, by observing histograms of the urine flow, the urologist or physician can usually detect the degree of prostrate enlargement and the necessary procedures to be undertaken to correct the disorder. In addition, post-operative urine flow data provides an excellent way of assessing the benefit achieved by surgery.

A variety of urine flow meters for providing urine flow data are presently commercially available. For example, mechanical urine flow meter devices usually comprise a container having a graduated scale for indicating the volume of urine within the container. Urine flow is detected by observing the change in volume as the patient voids into the container. Electrical urine flow meters for providing urine flow data have been developed. These devices may have a urine velocity-measuring apparatus in the form of a urine flow receptacle with a paddle wheel journaled therein. The paddle wheel is mechanically linked to a generator, which produces an output voltage, which is displayed on a voltmeter. The velocity of the urine stream impinging on the paddle wheel determines the paddle wheel velocity and therefore the output voltage of the generator. Other urine flow devices include a urine-receiving receptacle that has a pair of parallel spaced-apart rods or strips disposed therein. The rods or strips are electrically connected to a capacitance sensing circuit. As the volume of urine within the receptacle increases, the capacitance between the rods also increases so that by measuring the rate of change of the capacitance, an indication of the urine flow may be obtained.

As is apparent, current urine flow meters are complex and often require the assistance of a clinician for proper use; moreover, the devices require a high degree of maintenance. Furthermore, since urine contacts components in each of the meters, those components must be cleaned following each use. Therefore, a need exists for a reliable, low maintenance urine flow meter.

SUMMARY OF THE INVENTION

The present invention is based in part on the recognition that during urination (or voiding process) the unique characteristic sounds that are produced by the urine as it impacts the surface of the water in a toilet or urinal can be used to monitor the person's urinary flow pattern and its dynamics. Specifically, because the sound's intensity (loudness) and spectrum depend on the urine flow level, by detecting the intensity at selected acoustic frequencies, it is possible to accurately and precisely measure the urine flow rate.

In a preferred embodiment, the present invention is directed to techniques for analyzing urine flow and its dynamics by using sound levels that are detected at two or more distinct frequency regions or channels of the sound spectrum. One frequency region that is designated the measurement channel is where the sound measurement intensity or output strongly depends on urine flow levels. Another frequency region that is designated the reference channel is where the sound measurement intensity is not dependent on urine flow levels. By using a combination of measurements from the measurement channel and the reference channel, the urine flow monitoring apparatus of the present invention compensates for variations in operating conditions and other factors during use.

In one aspect, the invention is directed to an apparatus for measuring urine flow that includes:

a microphone for detecting acoustical sound that is generated as urine impacts a liquid surface and converting it into electrical signals;

an amplifier operatively coupled to the microphone to amplify electrical signals therefrom;

an analogue-to-digital converter for converting electrical signals into digital form;

a digital filter operatively connected to the analogue-to-digital converter for extracting filtered signals; and a signal processor for analyzing filtered signal components to generate urine flow level data.

In another aspect, the invention is directed a device for measuring urine flow that includes:

a transducer for detecting acoustical sound that is generated as urine impacts a liquid surface and converting it into electrical signals;

an amplifier to amplify the electrical signals;

an analogue-to-digital converter for converting the electrical signals into digital form;

a digital filter for extracting filtered signals; and means for analyzing signal components to generate urine flow level data.

In a further aspect, the invention is directed to a system for analyzing urinary flow patterns of a male patient as he voids that includes:

a transducer for converting, acoustic energy, that is generated as urine from the patient impacts a surface, into electrical signals;

an amplifier operatively coupled to the transducer to amplify electrical signals therefrom;

an analogue-to-digital converter for converting the electrical signals into digital form;

a digital filter operatively coupled to the analogue-to-digital converter for extracting filtered signals, and means for analyzing signal components to identify urinary flow patterns.

In yet another aspect, the invention is directed to a portable apparatus for measuring urinary flow patterns that includes:

(a) an audio peripheral that includes:

a transducer for converting acoustic energy, that is generated as urine from a patient impacts a surface, into electrical signals; and an amplifier operatively coupled to the transducer to amplify electrical signals therefrom;

(b); an analogue-to-digital converter for converting the electrical signals into digital form;

(c) a processing peripheral that includes:

a digital filter operatively coupled to the analogue-to-digital converter for extracting filtered signals; and means for processing signal components to generate signals that are representative of urinary flow data, wherein the analogue-to-digital converter is housed in the audio peripheral or in the processing peripheral.

In a still another aspect, the invention is directed to a method for measuring urinary flow from a male patient as he voids that includes the steps of:

(a) detecting acoustic energy that is generated as urine impacts a liquid surface;

(b) converting the acoustic energy into electrical signals;

(c) extracting filtered signals from the electrical signal with a digital filter; and (d) processing the filtered signals to generate output signals that represent urinary flow data for the male patient.

In a preferred embodiment of the urine flow-monitoring device yields urine flow data that is selected, from the group consisting of average flow rate, maximum flow rate, time to maximum flow level, flow dynamics, and combinations thereof.

DETAIL DESCRIPTION OF PREFERRED EMBODIMENTS

Figure 1:
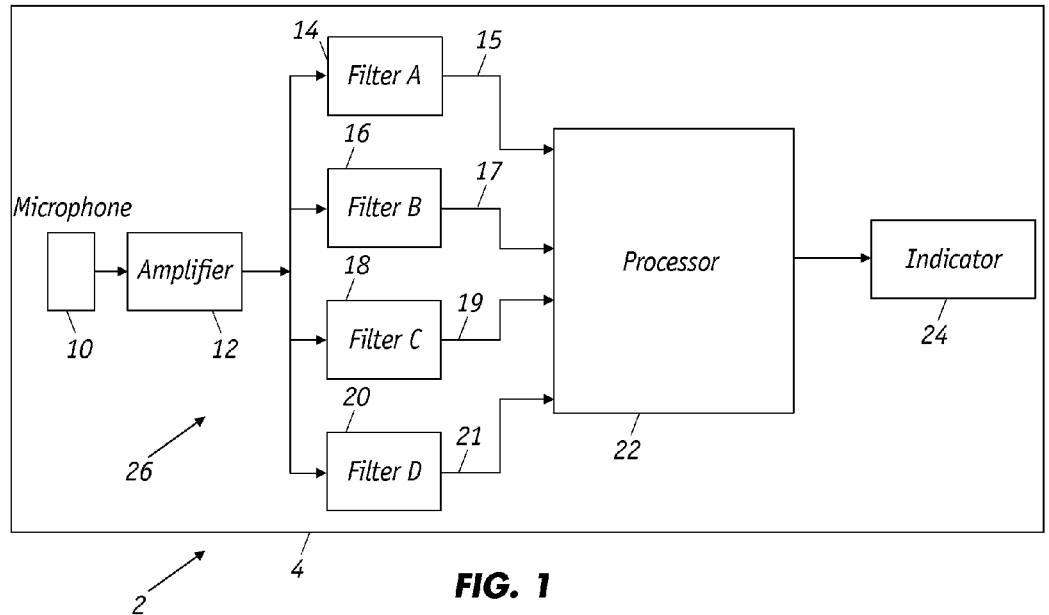
FIGS. 1 to 8 are schematics of alternative configurations of the urine flow monitoring device.

As shown in FIG. 1, the medical urine flow monitoring, device 2 includes a housing 4 that encloses a microphone 10, amplifier 12, a bank of filters 26 that includes filters 14, 16, 18, and 20, a signal processor 22 and an output indicator 24. Electrical signals from microphone 10, which can be omnidirecdonal or unidirectional microphone(s), are amplified by amplifier 12 before being passed through a plurality of filters 14, 16, 18 and 20, that produce filtered signals 15, 17, 19, and 21, respectively. As further described herein, the bank of filters 26 serves to select the filtered signals of the desired frequency ranges to be analyzed by processor 22. The filters comprise one or more of a high-pass, low-pass, band-pass, and band-stop filter, the example, which are designated as Filters A, B, C and D, respectively. FIG. 1 depicts a four-channel urine flow-monitoring device with each channel employing a different type of filter. As further described herein, preferably one or more of the channels measure sound level with frequencies in a measurement range and one or more of the channels measure sound level with frequencies in a reference range. The choice of filters depends on, among other things, the filtered frequencies of interest. The filters may be fixed or variable. Housing 4 can be constructed as a portable unit that can secured to a person's belt or it can be designed as a permanent wall unit that can be mounted on the bathroom wall at home, the hospital or doctor's office.

Figure 2:
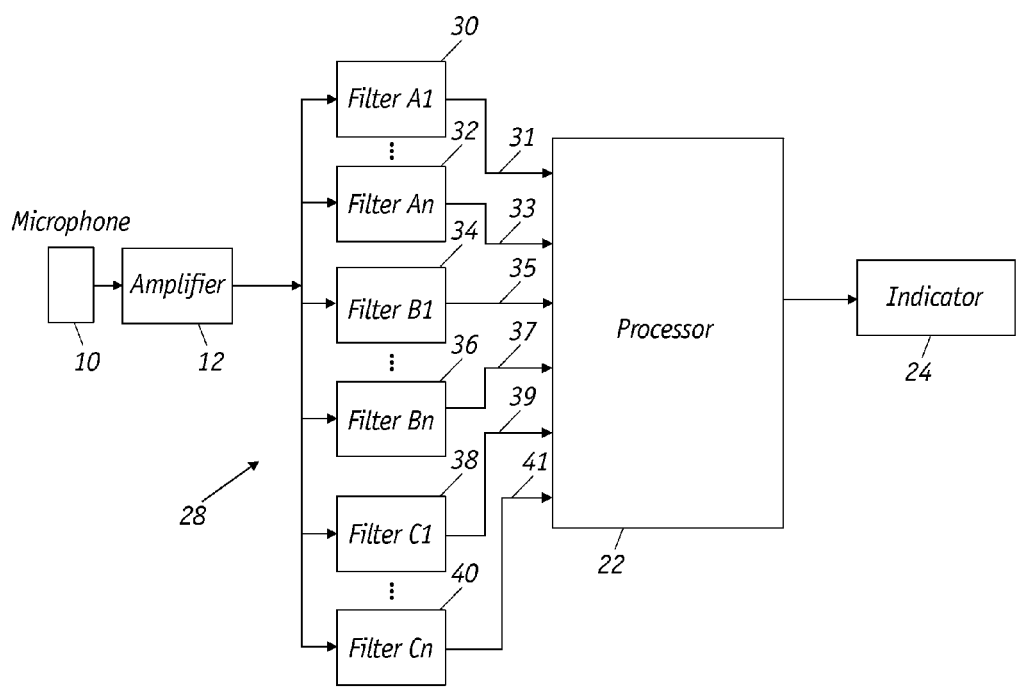

FIG. 2 depicts a multiple channel urine flow-monitoring device that includes a microphone 10, amplifier 12, a bank of filters 28, a signal processor 22 and an output indicator 24. This embodiment illustrates a device where multiple channels use the same type of filters, preferably with different frequencies of operation, and is expected to be more accurate than the device of FIG. 1. Filters 30 and 32, which produce filtered signals 31 and 33, respectively, employ filters of type A. Filters 34 and 36, which produce filtered signals 35 and 37, respectively, employ filters of type B. And finally, filters 38 and 40, which produce filtered signals 39 and 41, respectively, employ filters of type C.

Figure 3:
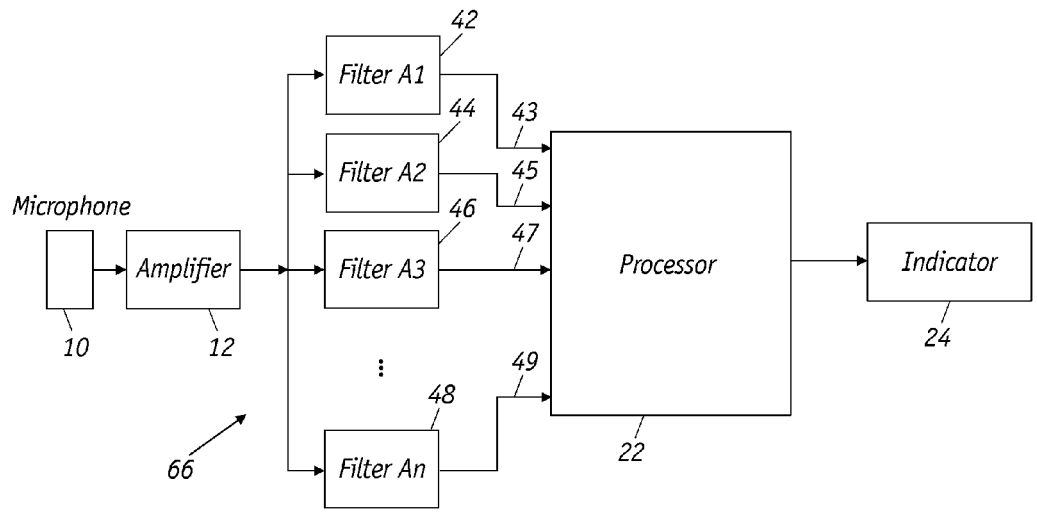

FIG. 3 depicts a multiple channel urine flow monitoring device that includes a microphone 10, amplifier 12, a batik of filters 66, a signal processor 22 and an output indicator 24. This embodiment illustrates a multiple channel device that uses the same type of filters. Specifically, filters 42, 44, 46, and 48, which produce filtered signals 43, 45, 47, and 49, respectively, each employs a filter of type A.

Figure 4:
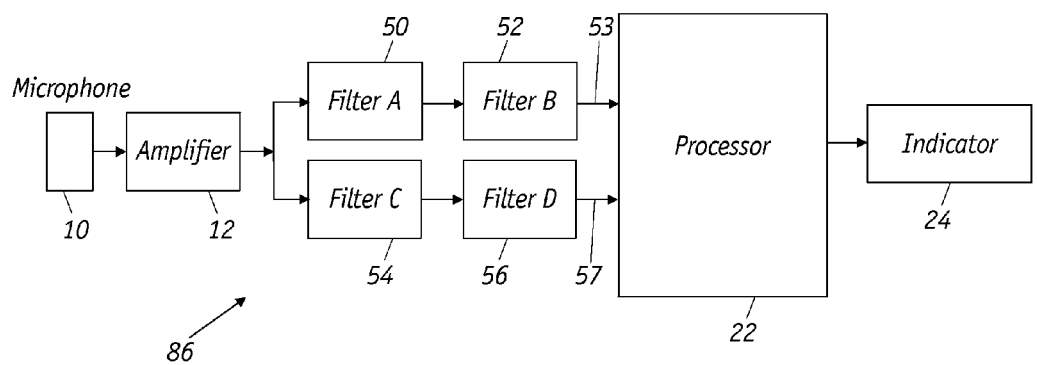

FIG. 4 depicts a multiple channel urine flow monitoring device that includes a microphone 10, amplifier 12, a bank of filters 86, a signal processor 22 and an output indicator 24. This embodiment illustrates a device where at least one of the channels uses two or more filters. Specifically, amplified signals are passed through two channels: the first comprising filters 50, 52 and the second comprising filters 54, 56, to produce filtered signals 53 and 57 that are processed by processor 22. Four different types of filters, designated A, B, C and D, are employed but it is understood different combinations of filters can be used.

Figure 5:
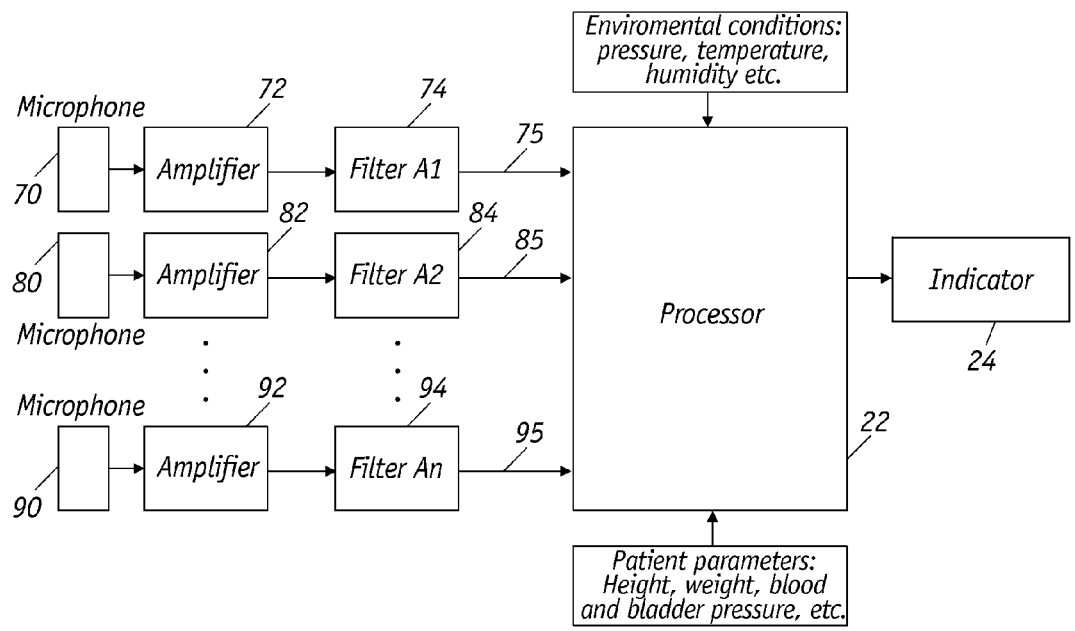

FIG. 5 depicts a multiple channel urine flow monitoring device that employs a microphone for each channel for improved performance. Each microphone can be configured for sound acquisition in a particular frequency range. Specifically the first channel includes microphone 70, amplifier 72 and filter 74; the second channel includes microphone 80, amplifier 82 and filter 84; and the third channel includes microphone 90, 92 and filter 94. Processor 22 analyzes filtered signals 75, 85, and 95 to generate programmed outputs that are displayed in indicator 24. Environment conditions such as pressure, temperature, humidity and other factors, such as urine receptacle geometry and size and water depth, that can influence the intensity and/or frequency of the sound detected are entered into processor 22. The patient's medical history including his height, weight, blood pressure, bladder pressure and other health parameters can also be entered into the processor.

Figure 6:
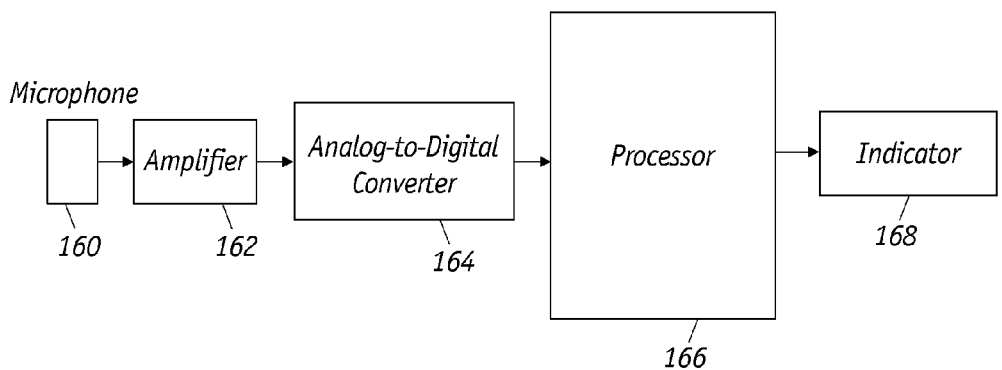

FIG. 6 depicts a urine flow monitoring device that includes a microphone 160, amplifier 162, an analogue-to-digital converter 164, a signal processor 166 and an indicator 168. The analogue-to-digital converter converts amplified microphone signal into digital form. The processor digitally filters the signal components of interest and generates outputs that are displayed by the indicator. As mentioned above, environment conditions and the patient's physical condition and medical history can be entered into the processor.

Figure 7:
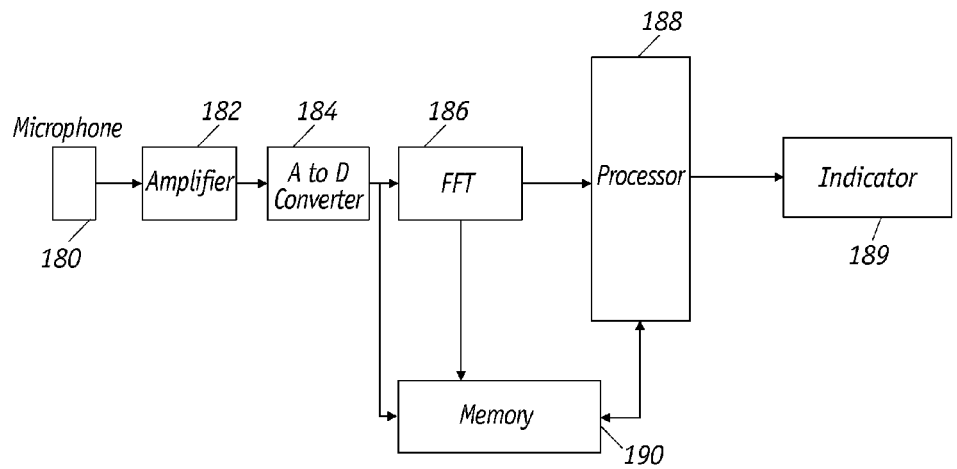

FIG. 7 illustrates an embodiment of the medical urine flow monitoring device which is similar to that of FIG. 6 that incorporates a fast Fourier transform (FFT) unit 186. Specifically, the device includes a transducer 180, such as a microphone, an amplifier 182, analogue-to-digital (A/D) converter 184, signal processor 188 and indicator/display unit 189. FFT 186 produces digital signals representing the data in a plurality of frequency ranges. These signals in turn are processed by processor 188 that calculates various urine flow parameters, which are visually presented in indicator/display unit 189. The device can also include memory 190 for storing raw digitized signals, spectrum information in the frequency ranges of interest, filtered signals, and calculated void process parameters.

Figure 8:
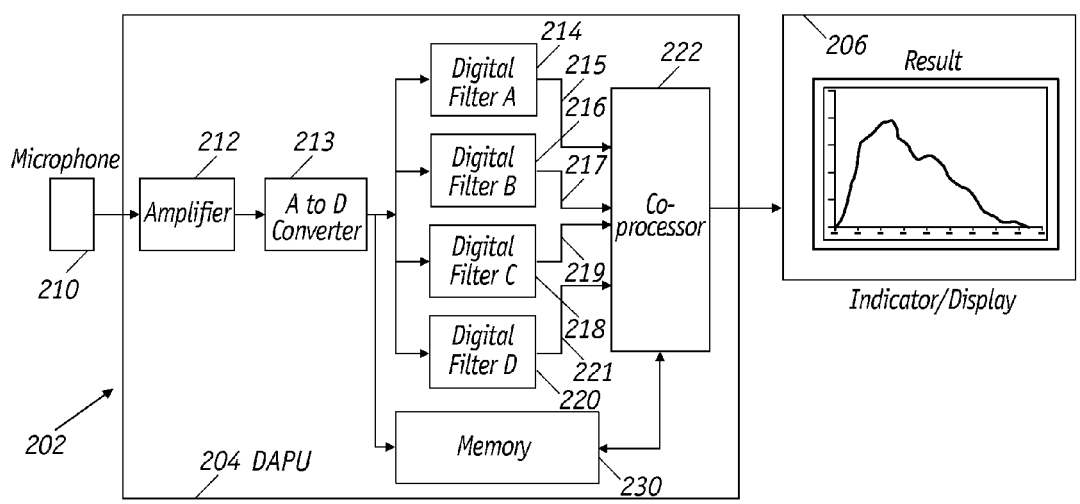

Components that form the medical urine flow monitoring device of the present invention can be incorporated in a single integral unit or they can be housed in separate stand-along peripherals or modules. For example, as shown in FIG. 8, the medical urine flow monitoring device 202 includes a transducer 210, a data acquiring and processing unit (DAPU) 204, and output indicator/display unit 206. DAPU 204 includes an amplifier 212, analogue-to-digital (A/D) converter 213, a bank of filters that includes digital filters 214, 216, 218, and 220, and signal co-processor 222. Each digital filter can be selected from the group consisting of a high-pass, low-pass, band-pass, and band-stop filter, for example, which are designated as Filters A, B, C and D, respectively. While the bank of four filters is illustrated as having four different types of filters, it is understood that the filters can he of the same type or different types. Transducer 210, such as a microphone, converts sound to electrical signals that are amplified by amplifier 212. Output signals from amplifier 212 are converted into digital signals by A/D converter 213 before being processed by the plurality of filters 214, 216, 218 and 220 that produce filtered signals 215, 217, 219, and 221, respectively. The hank of filters serves to select the filtered signals of the desired frequency ranges to he analyzed by co-processor 222 which processes the filtered signals and calculates the flow level and void process parameters, such as the maximum and average flow levels, time duration of urination from beginning to its maximum level and total voided urine volume. Results of the calculations, including dynamic flow-time dependence data, are visually presented in indicator/display unit 206, which can comprise a light-emitted diode, liquid crystal or other displays.

As an option, DAPU 204 can include memory 230 for storing raw digitized signals, filtered signals, and calculated void process parameters. The stored information can be retrieved from the memory, processed through the filters and displayed as needed. The data can also be compared to the latest test results to evaluate trends in the urine flow dynamics. The DAPU 204 can he constructed as a dedicated urine flow monitoring peripheral device that has a built-in microphone 210. Alternatively, the microphone is housed in a separate audio peripheral device that can be operatively coupled to the DAPU peripheral device via a cable or by wireless communication. FIG. 8 depicts the amplifier 212 and A/D converter 213 as being housed in the DAPU but it is understood that the amplifier or both the amplifier and A/D converter can be housed with the microphone as part of the audio peripheral device. Likewise, the indicator/display can be housed together with the DAPU or all the components of the urine flow monitoring device can be housed in a single housing.

The device of the present invention as illustrated in FIGS. 6, 7 and 8 can employ, for instance, logarithmic or linear amplifiers. If the urine flow monitoring device has a logarithmic amplifier and is configured to process sound levels in decibels, its amplified signals are passed through the measurement and reference channel filters and the difference in the decibel readings is calculated, signal components are stored, analyzed, and converted by the co-processor's into signals for the indicator or display. It should be noted that in operation preferably readings are continuously derived from both the measurement and reference channels from the beginning to the end of the voiding process, stored and then processed to yield information about the patient's urine flow pattern and to provide an evaluation of the patient's condition.

In the case where the urine flow monitoring device has a linear amplifier and is configured to process sound levels in linear units, its amplified signals are passed through the measurement and reference channel filters and the ratios of the filtered signal readings are calculated, signal components are stored, analyzed, and converted by the co-processor into signals for the indicator or display.

One method of calibrating the urine flow-monitoring device is to measure the sound with the measurement channel and reference channel at different urine flow rates under controlled flow conditions. Another method is based on the total urine volume voided during the calibration. For example, as the flow impacts the water in a toilet, the urine flow monitoring device captures the sound and records the corresponding sound levels of the measurement channel $M(t)$ and reference channel $R(t)$. The output signal. Which is calculated as the difference between the measurement and reference channels: $D(t)=M(t)-R(t)$, and which is proportional to the flow rate is calibrated with respect to the total urine volume $V_0$. It is known that the area under the function $D(t)$ corresponds to the total urine volume $V_0$, which cart be calculated by the equation $V_0 = \int_{t_1}^{t_2}(A \cdot D(t)+B)dt$, where A and B are the calibration coefficients, and $t_1$ and $t_2$ are times of the beginning and the end of the urination process. Thus, calibrating, the device only requires that coefficients A and B be determined. If as linear amplifier is used, the total voided urine volume is calculated as $V_0 = \int_{t_1}^{t_2}(C \cdot F(t)+D)dt$, where $F(t)$ is the ratio between measurement signal $M(t)$ and reference signal $R(t)$: $F(t)=M(t)/R(t)$, and C and D are the calibration coefficients. Polynomial dependencies of the higher order, if needed, can also be used to calibrate the device. As is apparent, the urine flow-monitoring device can employ multiple measurement channels and multiple reference channels and the output signals derived from each device can be similarly calibrated.

Environmental conditions such as temperature and pressure can affect measurements of the urine-flow monitoring device. A device can be calibrated under different conditions at the factory so that when a patient uses the device he can set the appropriate operating, conditions of temperature, pressure etc. so that the correct calibration constants are used.

The DAPU peripheral device can be connected to a display apparatus 206 (FIG. 8) that is in the form of a portable computer that includes, fir example, a notebook., laptop, mobile computer, cell phone, smart phone, internet device, and the like. The connection between the DAPU and portable computer can also be through a cable using designated ports or by wireless technology. The DAPU output can be configured to be in analogue or digital form consisting of raw or processed signals. For example, a smart phone can be equipped with the requisite software application to process and display test results.

Figure 9:
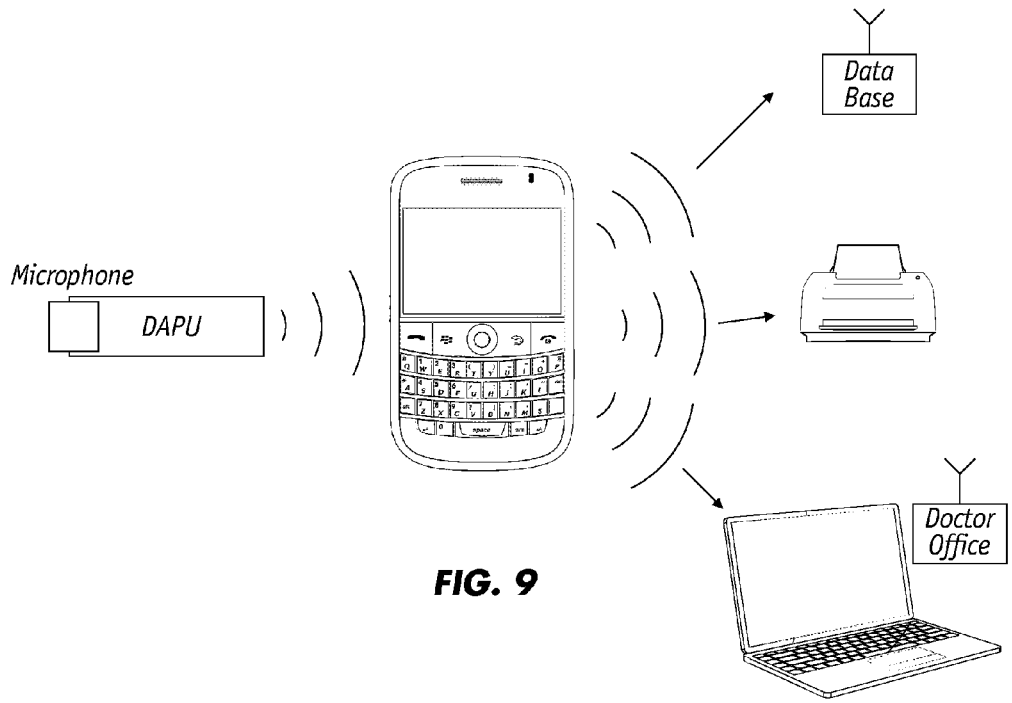
FIG. 9 illustrates the operations of a urine flow monitoring device transmitting data.

FIG. 9 illustrates a portable apparatus for measuring, urinary flow patterns that includes an audio peripheral device that includes a microphone and a processing peripheral device that includes a DAPU. In this embodiment, the audio peripheral includes a microphone that is embedded in the processing peripheral to form an integral unit. A smart phone is configured to receive signals from the DAPU. The microphone/DAPU assembly can be secured to an article of clothing such as a belt. In operation, the DAPU acquires and process signals generated during a voiding process. The processed information is transmitted via "blue tooth" or other wireless protocol to the smart phone simultaneously during, the voiding process. Test results can be displayed immediately after the voiding process or, being retrieved from the memory, at a later convenient time. In addition, the patient can transmit the data from the smart phone to a data base, peripheral printer, doctor's office, or other remote receiver.

It is contemplated that the DAPU can be incorporated into a smart phone or other portable computer device, which can be programmed to acquire, filter and process sound information to generate urine flow dynamics data during voiding.

Figure 10:
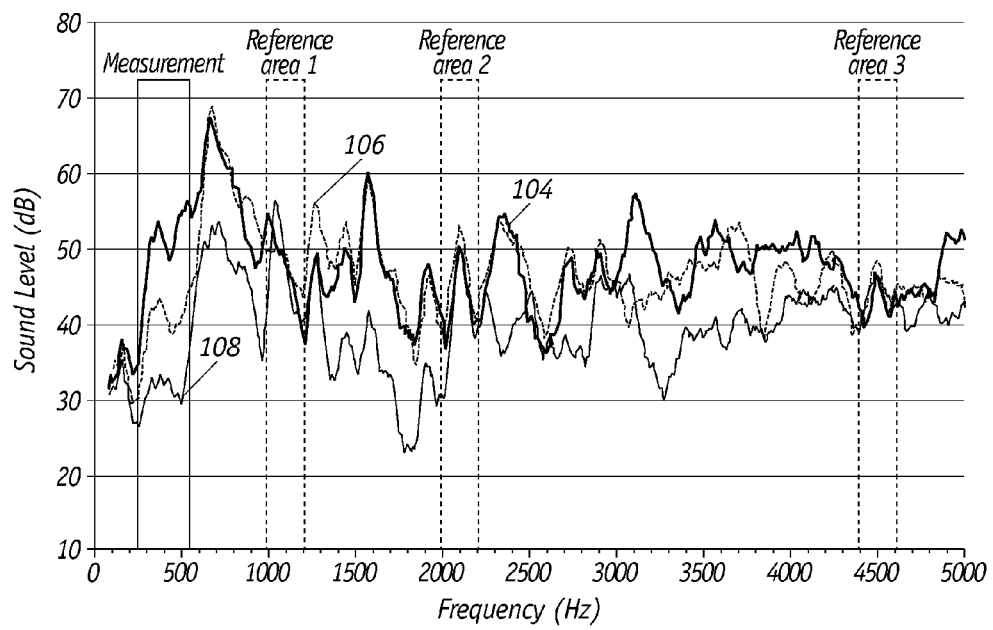
FIG. 10 is a graph of sound spectra (loudness in decibel vs. frequency) that are generated by the impact of urine on water.

When a male patient urinates, a continuous, distinctive sound is produced as the urine impacts the water in the toilet. Three representative sound spectra captured by a microphone during urinations are presented in FIG. 10. Spectrum 104 depicts the measured response in the case where the urination exhibited "strong" volumetric flow, spectrum 106 was the response for "medium" volumetric flow, and spectrum 108 was the response for "weak" volumetric flow. As is apparent, the sound level signal in the frequency range of 250-550 Hz, which is designated a measurement range, strongly depends on a flow level, whereas the sound level signals in the frequency ranges of 1000-1200 Hz, 2000-2200 Hz, and 4400-4600 Hz, which are designated as reference ranges, are significantly less so. Thus, by monitoring the loudness of the sound caused by urination at a frequency where the measured sound level depends on the flow level, it is possible to measure the urine flow rate. The intensity of the sound that is acquired by the microphone is influenced by a number of extraneous factors including the relative position and distance of the microphone to the site of impact as well as environmental conditions. Thus, in a preferred embodiment, the urine flow monitoring device has at least two channels: one or more measurement channels that measures sound at a frequency within the range of 250-550 Hz and one or more reference channels that measures sound at a frequency within the range of 1000-1200, Hz 2000-2200 Hz, and/or 4400-4600 Hz. As described further herein, by analyzing the difference between the decibel values of the measurement and reference signals or the ratio between the measurement and reference signals, the urine flow rate and other data can be determined in a manner wherein measurement variations caused by the extraneous factors are significantly reduced or eliminated. The urine flow-monitoring device can use one or more of the reference ranges.

A urine flow monitoring device consisting of a transducer device that was coupled to a laptop personal computer, which was configured to perform digital filtering on raw data, was used to monitor urine flow and its dynamics. Specifically, a transducer assembly, which included a microphone, amplifier and A/D converter, was connected to computer via a USB connector. The computer included customized software program (LabVIEW from National Instruments of Austin Tex.) that performed digital filtering of microphone signals at measurement and reference frequencies and their processing. The measurement and reference filters were programmed as band pass filters with the range of 250-450 Hz for the measurement channel and 1000-1200 Hz for the reference channel 1 and 2000-2200 Hz for the reference channel 2. The computer also displayed the test results.

Figure 11:
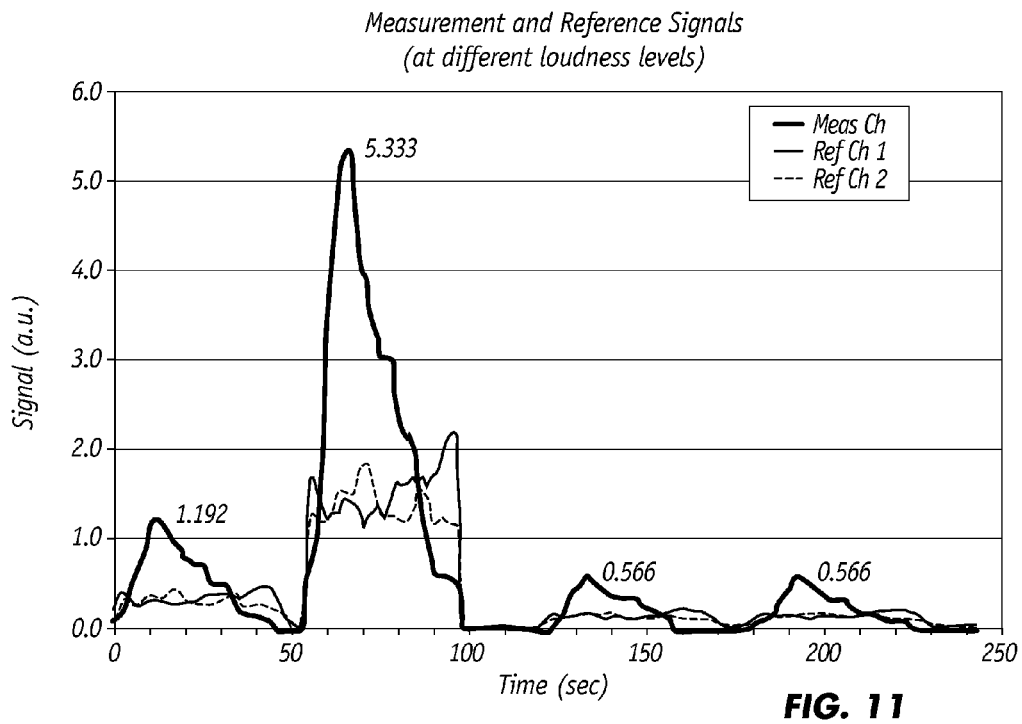
FIG. 11 shows the measured output signals from the measurement channel and two reference channels vs. time from a urine flow monitoring apparatus in detecting sound generated in a voiding process.
Figure 12:
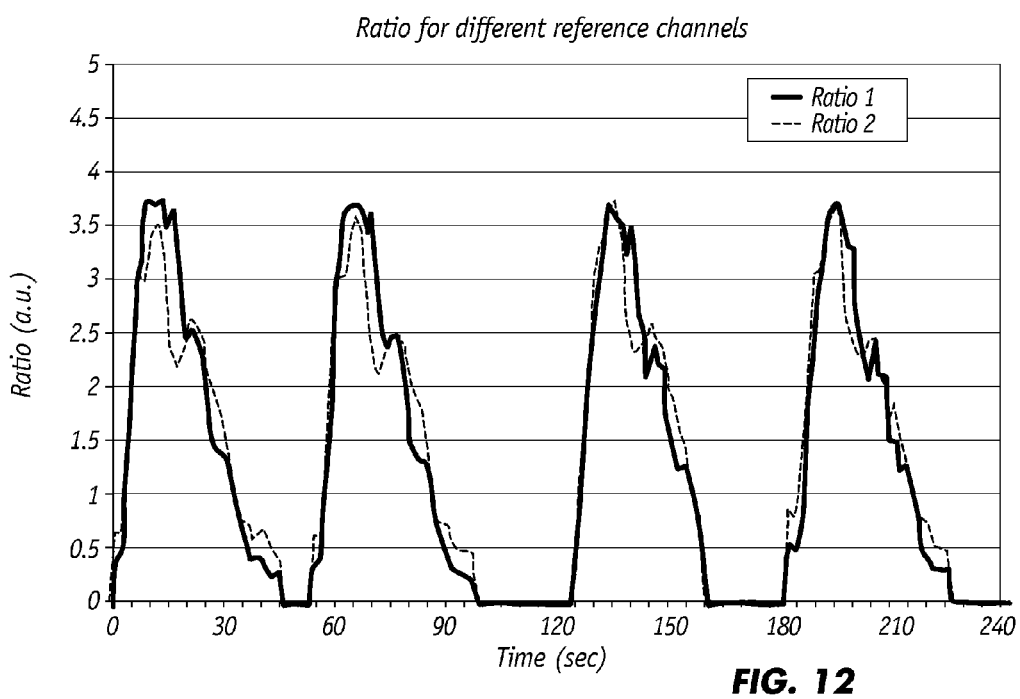
FIG. 12 depicts the ratios of measurement channel output to reference channel output vs. time for the urine flow monitoring data shown in FIG. 11.

To demonstrate device repeatability and the inventive technique's independence from the loudness of the voiding process, the sound pattern generated by a male urinating, into the water in a toilet was recorded. Thereafter, the same recorded sound pattern was reproduced repeatedly in succession at four different loudness levels for analysis with the urine flow monitoring device. The output signals as measured by measurement channel and reference channels 1 and 2 for each of the four runs are shown in FIG. 11. The loudness level for the second (and highest) sound pattern was about nine times that of the third (and lowest) sound pattern. Thereafter, the ratio of the output signals from the measurement channel and reference channel 1 (designated as ratio 1) and the output signals from the measurement channel and reference channel 2 (designated as ratio 2) were calculated during the voiding and are presented in the FIG. 12. As is evident, the contours of the dependencies for all four samples are very similar and their amplitudes are very similar as well.

Figure 13:
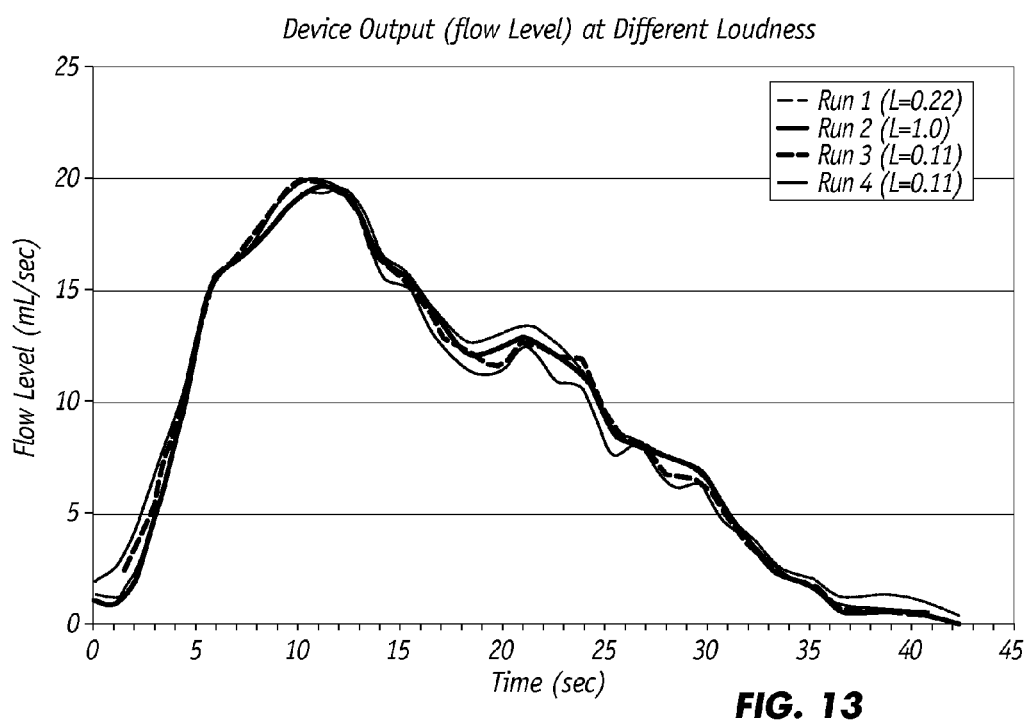
FIG. 13 presents the calibrated urine flow rate vs. time.

The device was calibrated based on the total void urine volume which was about 380 mL. Calibration was applied to the average flow ratio, which was calculated based on ratio 1 and ratio 2 presented in FIG. 12. Calibrated urine flow level dependencies for each of the four runs are presented in FIG. 13. As is apparent, the four dependencies are extremely close to each other. This demonstrates that the feature of the invention of employing the ratio between measurement and reference channels effectively eliminates the dependence on the loudness of the monitoring voiding process and position of the microphone. This significantly increases reliability and accuracy of the measurement As is evident from the graph, the maximum flow rate was between 19 mL/sec and 20 mL/sec and occurred approximately 11 to 12 seconds into the urination process. The average urine flow rate was about 9.2 mL/sec.

The urine-flow monitoring device can be programmed with data to enable the unit to display urinary flow information, based on analysis and classification, for the user. For example, analysis of the filtered signals can yield information concerning the patient's voiding patterns, including: flow dynamics, maximum urine flow rate (which may be indicative of the level of urinary tract blockage, if any), average urine flow rate, and time to maximum flow level. The filtered signals can be correlated to urine flow levels. In order to customize this information, the patient's height, weight, body mass index, blood pressure and other data of his medical history can be uploaded into the processor. A database of urine flow data generated by patients who are classified a being healthy as well as front those who are suffering from various conditions that result in abnormal urine flow can be stored in the processor's calibration circuit. Once a patient's voiding patterns are established with the device, they can be compared to voiding patterns in the database and appropriate information displayed.

The foregoing has described the principles, preferred embodiment and modes of operation of the present invention. However, the invention should not be construed as limited to the particular embodiments discussed instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method for measuring urine flow comprising the steps of:
    detecting acoustical sound that is generated as urine impacts a liquid surface and converting the acoustic sound into an electrical signal;
    converting the electrical signal into a digital signal;
    digitally filtering the digital signal in a measurement channel and a reference channel wherein extracted filtered signals from the measurement channel are sensitive to urine flow levels and extracted filtered signals from the reference channel are insensitive to urine flow levels; and
    analyzing the extracted filtered signals from each of the measurement channel and the reference channel to generate urine flow level data that is a measurement of at least one real time urine flow parameter.

2. The method for measuring urine flow of claim 1 wherein extracted filtered signals from the measurement channel have frequencies in the range from 250 to 550 Hz.

3. The method for measuring urine flow of claim 1 wherein extracted filtered signals from the reference channel have frequencies in the range of 1000 to 1200 Hz, 2000 to 2200 Hz, and/or 4400 to 4600 Hz.

4. The method for measuring urine flow of claim 1 wherein the detecting step includes detecting the acoustic sound with a microphone, the microphone converting the acoustic sound into the electrical signal.

5. The method for measuring urine flow of claim 1 wherein the detecting step includes the steps of:
    detecting the acoustic sound with a plurality of microphones, each of the microphones converting the acoustic sound into analog signals; and
    combining the analog signals into the electrical signal.

6. The method for measuring urine flow of claim 1 wherein the detecting step includes detecting the acoustic sound with a transducer, the transducer converting the acoustic sound into the electrical signal.

7. The method for measuring urine flow of claim 1 further comprising the step of amplifying the electrical signal prior to the converting step.

8. The method for measuring urine flow of claim 1 wherein the digitally filtering step further includes filtering the digital signal into a plurality of measurement channels and a plurality of reference channels.

9. The method for measuring urine flow of claim 8 wherein the filtering the digital signals into a plurality of measurement channels and a plurality of reference channels step includes applying the digital signal to a digital filter in each respective one of the measurement channels and the reference channels, each digital filter developing one of the extracted filtered signals.

10. The method for measuring urine flow of claim 8 wherein each of the measurement channels is associated with a respective one of the reference channels.

11. The method for measuring urine flow of claim 1 further comprising the step of storing the urine flow level data in electronic memory.

12. The method for measuring urine flow of claim 1 further comprising the step of transmitting the urine flow level data to a receiver remote from the liquid surface.

13. The method for measuring urine flow of claim 1 further comprising the step of transmitting the urine flow level data to an indicator device which develops a visual indication of the at least one of the urine flow level data.

14. The method for measuring urine flow of claim 1 wherein the at least one urine flow parameter is a selected one of average flow rate, maximum flow rate, time to maximum flow level, voided volume, void time, and combinations thereof.

15. A method for measuring in real time urine flow parameters of a urination event from acoustical sound developed as urine impacts a liquid surface comprising the steps of:
    developing an electrical signal having an intensity indicative of a sound level of the acoustical sound developed from the urination event;
    filtering the electrical signal into a first filtered signal having a first frequency spectrum of the electrical signal and a second filtered signal having a second frequency spectrum of the electrical signal wherein the intensity of the electrical signal in the first frequency spectrum is substantially dependent on urine flow and the intensity of the electrical signal in the second frequency spectrum is substantially independent on urine flow; and
    developing an output signal as a function of the first filtered signal and the second filtered signal, the output signal being commensurate with a quantitative measurement of at least one of the urine flow parameters.

16. The method for measuring in real time urine flow parameters of claim 15 further comprising the steps of applying the output signal to an indicator device which develops a visual indication of the at least one of the urine flow parameters as a function of the output signal.

17. The method for measuring in real time urine flow parameters of claim 15 wherein the electrical signal is developed as an analogue electrical signal.

18. The method for measuring in real time urine flow parameters of claim 17 wherein the electrical signal is developed by at least one microphone.

19. The method for measuring in real time urine flow parameters of claim 17 wherein the filtering step includes the steps of:
    converting the electrical signal to a digital signal; and
    applying the digital signal to a digital filter in a first spectrum channel and to a digital filter in a second spectrum channel to develop respectively the first filtered signal as a first filtered digital signal and the second filtered signal as a second filtered digital signal.

20. The method for measuring in real time urine flow parameters of claim 19 wherein the at least one digital filter in one of the first spectrum channel and the second spectrum channel is a selected one of a band pass filter, a band stop filter, a high pass filter and a low pass filter.

21. The method for measuring in real time urine flow parameters of claim 15 wherein the output signal developing step develops the output signals as a ratio between the first filtered signal and the second filtered signal.

22. The method for measuring in real time urine flow parameters of claim 15 wherein the at least one of the urine flow parameters is selected one of instantaneous flow rate, average flow rate, maximum flow rate, time to maximum flow rate, and flow dynamics.

23. The method for measuring in real time urine flow parameters of claim 15 wherein the filtering step further includes filtering the electrical signal into a third filtered signal haying a third frequency spectrum of the electrical signal wherein the intensity of the electrical signal in the third frequency spectrum is substantially independent of the urine flow level, the method further comprising the steps of:
- obtaining a first ratio between the first filtered signal and the second filtered signal and a second ratio between the first filtered signal and the third filtered signal; and
- obtaining a first ratio between the first filtered signal and the second filtered signal and a second ratio between the first filtered signal and the third filtered signal to calibrated the output signal upon the time dependencies of the first ratio and the second ratio being substantially commensurate with each other.

\* \* \* \* \*